Figure 1:
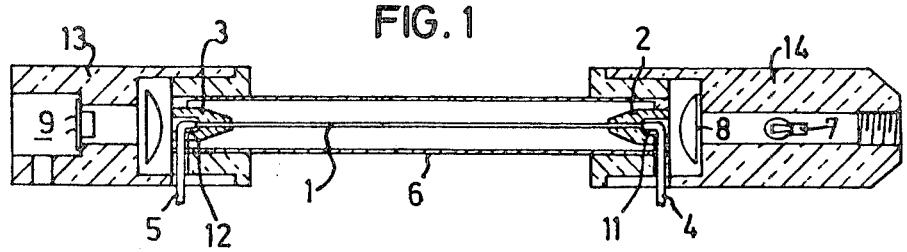

United States Patent [19]

Carlson

[11] Patent Number: 4,477,186
[45] Date of Patent: Oct. 16, 1984

[54] PHOTOMETRIC CUVETTE

[75] Inventor: Henning L. Carlson, Täby, Sweden

[73] Assignee: Bifok AB, Sollentuna, Sweden

[21] Appl. No.: 351,919

[22] Filed: Feb. 24, 1982

[51] Int. Cl.[3] ...................... G01N 21/05; G01N 21/85
[52] U.S. Cl. ...................................... 356/246; 356/410
[58] Field of Search ................ 356/410, 411, 440, 446

[56] References Cited

U.S. PATENT DOCUMENTS

| 3,370,502 | 2/1968 | Wilks, Jr. | 356/246 |
| 3,418,053 | 12/1968 | Pelavin | 356/410 |
| 3,433,570 | 3/1969 | Hansen | 356/128 |
| 3,770,350 | 11/1973 | Stone et al. | 356/246 X |
| 4,050,895 | 9/1977 | Hardy et al. | 356/445 |
| 4,190,363 | 2/1980 | Adrian | 356/246 |

FOREIGN PATENT DOCUMENTS 2420594 11/1975 Fed. Rep. of Germany.

*Primary Examiner*—Vincent P. McGraw
*Attorney, Agent, or Firm*—Poms, Smith, Lande & Rose

[57] ABSTRACT

Photometric cuvette for optical analysis of through-flowing medium, made as a thin and narrow transparent tube requiring minimum sample amounts. Light, substantially parallel to the tube length, is led obliquely into the tube through its wall, is reflected and led obliquely out through the tube wall to a detector. The angle of incidence is selected so that after entry, the light is totally reflected against the outer tube wall where the wall is in contact with surrounding atmosphere, the light being supplied essentially uniformly around the tube.

16 Claims, 3 Drawing Figures

PHOTOMETRIC CUVETTE

The present invention relates to a cuvette for continuous through-flow which produces a longitudinal flow of sample medium.

Cuvettes for continuous through-flow can be made of glass tubes, the ends of which are bent or curved at the inlet and outlet. Such a cuvette provides good laminar flow, but it is not possible to obtain optimum optical properties in the bent or curved glass at the ends of the cuvette, where the light enters and exits. A portion of the light is absorbed in the ends walls or is refracted into the glass instead of passing axially through the cuvette. Nor it is possible to obtain uniformity in the curved end walls or to make two cuvettes identically the same.

A method of improving the optical properties of through-flow cuvettes is to make planar end windows in the cuvettes in which the inner and outer surfaces of the window are parallel and perpendicular to the longitudinal axis of the cuvette tube.

This design reduces the problem of refraction over curved cuvette ends and makes better uniformity of the cells possible. In order to obtain sufficient amounts of light, the light source is dimensioned so that the entire inlet opening is filled up, and at the same time the tube diameter is made relatively large. This design requires however large sample amounts. A further disadvantage of through-flow cuvettes provided with windows is the sharp angles formed at the tube ends.

The purpose of the present invention is to achieve a cuvette for continuous through-flow which requires very small sample amounts, which makes rapid, precise and readily reproducible results possible, which uses the light efficiently, which can be easily adapted to varying conditions, concentrations color strength in the sample, etc. and which is sturdy and inexpensive.

Figure 2:
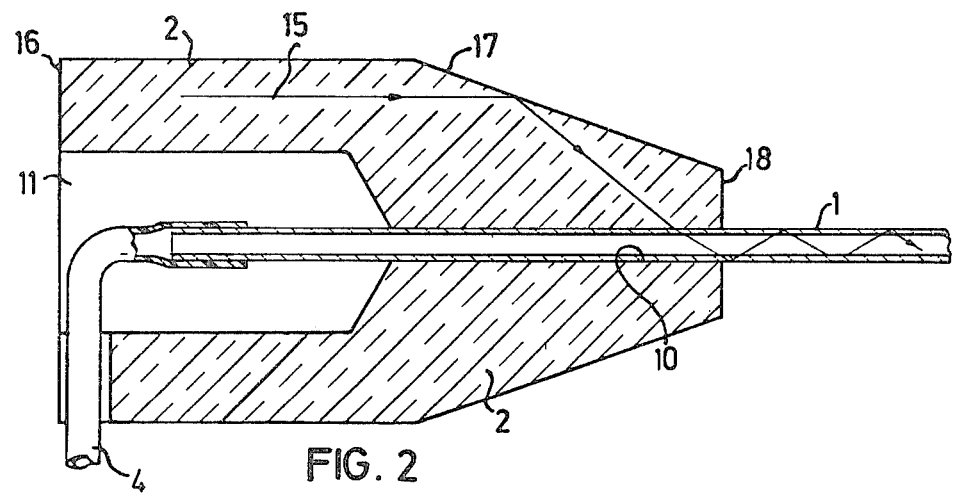
Figure 3:
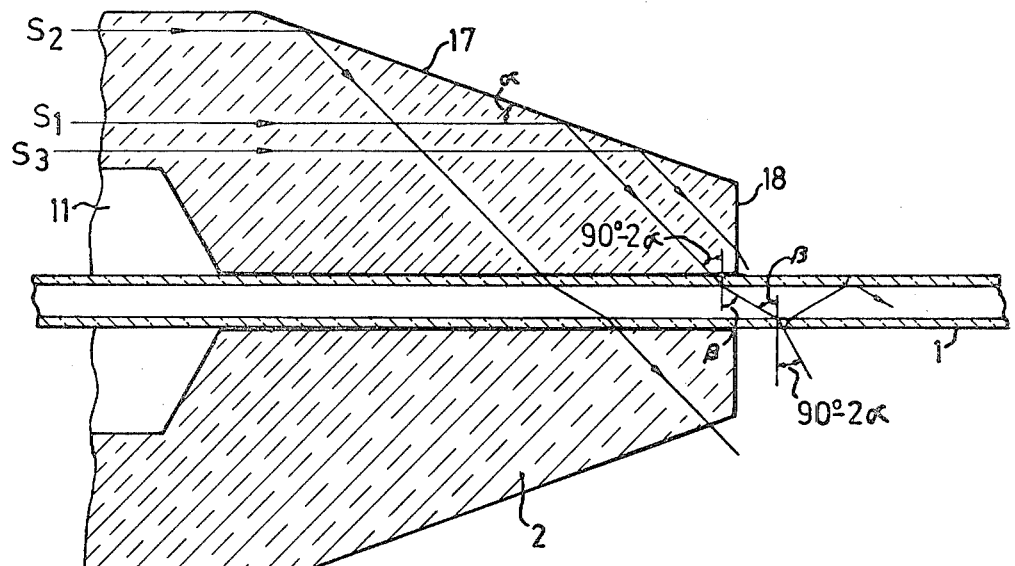

The cuvette according to the invention will be described in more detail with reference to the accompanying drawing, of which FIG. 1 shows a cuvette according to the invention in longitudinal section, FIG. 2 shows an enlarged section of one end of the cuvette, and FIG. 3 shows an end portion with light beams and paths drawn in.

The sample solution to be analyzed is conducted through a cuvette tube 1 of transparent material, fixed between two end portions 2,3. Inside the end portions, the tube is connected to an inlet tube 4 and outlet tube 5 for the solution. The end portions are fixed in the ends of a pipe 6 which acts as a frame. A lamp is arranged in a lamp housing 7 in front of one end of the pipe 6, with an optical system 8 for providing light parallel to the longitudinal axis of the tube 1.

At the other end of the pipe 6 behind the end portion 3 there is a measuring device 9, usually a photocell, for registering the light.

FIG. 2 shows the end portion 2 enlarged, with the path which the light follows.

The end portions 2,3 are identical and are made of transparent material, e.g. plastic, glass or the like in the form of a truncated cone. In the center of the truncated cone there is a hole 10 in which the cuvette tube 1 is fitted. Optical contact is made between the cone and the tube in a known manner with immersion oil or by fusion. The outer portion of the truncated cone is cut to cylindrical form with such a diameter that it fits into the pipe 6. A cavity 11 or 12 respectively is cut into this cylindrical portion, and in this cavity the cuvette tube 1 is jointed to the inlet 4 or outlet 5 respectively, which are hoses for example. The end portions 2,3, the frame pipe 6, the lamp and the lamp housing 7, the measuring device 9 and any additional mounting components are held together by two end sleeves 13,14.

The light from the light housing 7 and the optical system 8 is shown as a bundle of light rays 15 in FIG. 2 and enters the end portion 2 perpendicular to the rear ring surface 16. The light passes up to the conical lateral surface 17 on the end portion where the light rays are reflected, by virtue of proper selection of the angle of taper of the cone, and are directed into the sample solution through the tube wall 1.

In our work up to now, we have for the most part used plexiglass in the end portions, and a cuvette tube of glass, and the apparatus is described in connection with the use of these materials even if other transparent materials can of course be used. The entire apparatus can thus be made in glass, quartz etc. as the situation requires.

The ray paths are shown in greater enlargement in FIG. 3.

At an angle of taper $\alpha$, a ray $s_1$ parallel to the longitudinal axis of the cone will be totally reflected by the lateral surface of the truncated cone and, without refraction, go through the end portion and the wall of the cuvette tube 1 where it is refracted upon entering the liquid in the tube 1 at an angle of incidence which is $90° - 2\alpha$ and a refracted angle in the solution which is $\beta$. As is customary, the angles are in relation to the normal to the longitudinal axis of the device. The rays of light pass at an angle through the solution, strike the opposite interior wall of the tube at an angle $\beta$, are refracted, strike the outer wall of the tube at an angle of incidence $90° - 2\alpha$, and are totally reflected. In this manner, the light proceeds in a zigzag path through the cuvette tube. The material in the end portions and the cuvette tube, and the angle of taper $\alpha$, must be selected so that $n \times \sin(90° - 2\alpha)$ is greater than 1 in order for there to be total reflection at the boundary surface between the material and air.

A light ray $s_2$ farther away from the central axis is reflected so that the ray goes through the cuvette tube to the outer wall of the tube which is still inside the end portion. By virtue of the fact that the tube and the end portion have approximately the same index of refraction and are in optical contact, the ray continues in virtually the same direction out into the end portion and exits through the lateral surface 17 of the cone.

In a similar manner, light rays which are too close to the center will, after being reflected by the lateral cone surface 17, be directed against the top surface 18 of the truncated cone and pass through it.

The light which properly enters the end portion is reflected into the cuvette tube, is reflected inside the same a number of times and then passes out into the end portion 3, is reflected against the lateral cone surface 17 and is thrown as a bundle of rays, parallel to the longitudinal axis of the end portion, against the measuring device thereby providing the signals.

As was mentioned previously, the angle of taper $\alpha$ of the cone must be selected in conjunction with the index of refraction $n$ of the material in the end portions, so that $n \times \sin(90° - 2\alpha)$ is greater than 1.

The tube length of the cuvette is a matter of free choice, and when long cuvette tubes are required, the cuvette tube can be used in rolled form thus reducing the dimensions of the device.

The light source has not been described in more detail here. Rather, it has only been stated that a lamp with an optical system for providing parallel light is used. Lamps with various light compositions, monochromatic light etc. can be used, and it is also possible to use a laser as a light source with advantage.

With the cuvette according to the invention, an ideal continuous liquid flow is obtained without any sharp angles giving rise to turbulence or the like. By virtue of the fact that the cuvette tube can be made very narrow, the required sample amounts can be reduced to a minimum. For example, with a tube diameter of 0.25 mm a volume of only 0.5 μl/cm is required; i.e. with a tube as long as 1 m only 50 μl are required to fill the same.

It is also possible to empty and clean the tube with a cleaning brush, e.g. a plastic monofilament, or with air bubbles which are pressed through; something which was not possible in previous constructions with sharp curves and elbows. It should be mentioned in this connection that it is also possible to work with air-segmented solutions without removing the air bubbles prior to measurement.

In photometric analysis with the cuvette according to the invention, the proportion of light absorbed in passage through the sample is measured. It is expressed as the absorbency:

$$A = \log_{10}(I_o/I)$$

where $I$ and $I_o$ designate the light intensities registered by the detector when the cuvette is filled with sample solution or a reference solution respectively. When measuring fluorescence, excitation light can be sent through one end cone and the emitted light can be extracted through either one of the end cones. A blocking filter is used to separate the excitation light from the emitted light. It is also possible to irradiate the capillary cuvettes with excitation light through the lateral surface in the air between the end cones and take out the emitted light through one or both of the end cones. In this case it is not necessary to use the blocking filter. In nephelometric measurement the sample is also irradiated through the lateral surface of the cuvette tube, and the deflected, scattered light is taken out through one or both of the end cones.

What I claim is:

1. Method of optical analysis is an unobstructed flow-through cuvette wherein the medium is conducted through a hollow cuvette tube having a tubular wall of transparent material, characterized in that light essentially parallel to the longitudinal axis of the cuvette tube is directed obliquely into the tube through the tube wall adjacent one end of said tube, is reflected within said tube and travels to the other end of said tube where it is directed obliquely out through the tube wall to a detector, the angle of incidence of the light to the surface of the tube being selected so that the light is totally reflected after entry into the tube against the outer tube wall where said wall is in contact with the surrounding atmosphere, and that the light is supplied essentially uniformly around the circumference of the tube.

2. Method according to claim 1, characterized in that the light is totally reflected against the outer tube wall a plurality of times.

3. Method according to claim 1 or 2, characterized in that the light used is parallel, that it is first directed into a body of transparent material perpendicular to a boundary surface of the body, and that it is reflected against a concial portion of the lateral surface of the body, whereafter it is directed obliquely towards another boundary surface of the body in optical contact with the wall of the cuvette tube, whereby the light can pass into the flowing medium.

4. Method according to any one of claims 1 or 2, characterized in that the flow is halted during the actual measurement.

5. Method according to claim 3 characterized in that the flow is halted during the actual measurement.

6. A method according to claim 3, characterized in that the cuvette tube has an inner diameter which is less than 5 mm, preferably less than 1 mm and suitably between 0.2 and 0.4 mm.

7. A method according to claim 4, characterized in that the cuvette tube has an inner diameter which is les than 5 mm, preferably less than 1 mm and suitable between 0.2 and 0.4 mm.

8. A method according to claim 5, characterized in that the cuvette tube has an inner diameter which is less than 5 mm, preferably less than 1 mm and suitable between 0.2 and 0.4 mm.

9. A cuvette for optical analysis of through-flow medium comprising:
   a transparent cuvette tube having a first end, a second end and a tubular wall defining an unobstructed medium measurement zone with a longitudinal axis;
   means for introducing light obliquely through the cuvette wall uniformly around the circumference of said wall and adjacent said cuvette first end at an angle relative said wall such that said light, after passage through said wall, is reflected inward by said tube wall and contained within said medium measurement zone;
   means associated with said cuvette second end for directing said light obliquely out of said measurement zone uniformly around the circumference of said wall and directing said light to measurement means for measuring the amount of light which passes through said measurement zone from said first cuvette end to said second cuvette end.

10. Cuvette according to claim 9, wherein said means for introducing light into said cuvette tube and directing light out of said cuvette tube includes transparent end portions wherein the transparent materials in the end portions and in the cuvette tube, preferably glass, quartz or plastic such as plexiglass, have the same index of refraction.

11. Cuvette according to claim 9 or 10, characterized in that the end portions have the form of truncated cones with a base surface, a lateral surface and a top surface.

12. Cuvette according to claim 11, characterized in that the angle of taper of the cone is small, preferably 15°–30° and suitably about 19°.

13. Cuvettte according to claim 1 or 2 or 9 or 10, characterized in that the cuvette tube has an inner diameter which is less than 5 mm, preferably less than 1 mm and suitably between 0.2 and 0.4 mm.

14. Cuvette according to claim 11, characterized in that the cuvette tube has an inner diameter which is less than 5 mm, preferably less than 1 mm and suitable between 0.2 and 0.4 mm.

15. Cuvette according to claim 12, characterized in that the cuvette tube has an inner diameter which is less than 5 mm, preferably less than 1 mm and suitable between 0.2 and 0.4 mm.

16. A cuvette according to claim 9 including means for introducing medium into said cuvette tube first end and means for removing medium from said cuvette tube second end.

* * * * *